United States Patent [19]
Chobanian et al.

[11] Patent Number: 6,139,847
[45] Date of Patent: Oct. 31, 2000

[54] COMBINED USE OF ANGIOTENSIN INHIBITORS AND NITRIC OXIDE STIMULATORS TO TREAT FIBROSIS

[75] Inventors: Aram Chobanian, Natick; Peter Brecher, West Newton, both of Mass.

[73] Assignee: Trustees of Boston University, Boston, Mass.

[21] Appl. No.: 08/801,512

[22] Filed: Feb. 18, 1997

Related U.S. Application Data

[62] Division of application No. 08/482,819, Jun. 7, 1995, Pat. No. 5,645,839.

[51] Int. Cl.⁷ ..................................................... A61K 9/00
[52] U.S. Cl. ............................................ 424/400; 514/310
[58] Field of Search ............................... 424/400; 514/310

[56] References Cited

U.S. PATENT DOCUMENTS

| | | | |
|---|---|---|---|
| 4,954,526 | 9/1990 | Keefer | 514/611 |
| 5,264,447 | 11/1993 | Ohtawa | 514/381 |
| 5,268,358 | 12/1993 | Fretto | 514/12 |
| 5,278,192 | 1/1994 | Fung et al. | 514/645 |
| 5,304,541 | 4/1994 | Purchio et al. | 514/12 |
| 5,308,622 | 5/1994 | Casscells et al. | 424/422 |
| 5,312,621 | 5/1994 | Berman et al. | 424/85.7 |
| 5,326,559 | 7/1994 | Miller | 424/85.2 |
| 5,358,959 | 10/1994 | Halerpin et al. | 514/396 |
| 5,374,660 | 12/1994 | Murad et al. | 514/620 |
| 5,380,758 | 1/1995 | Stamler et al. | 514/562 |
| 5,382,587 | 1/1995 | Baldwin et al. | 514/278 |
| 5,385,937 | 1/1995 | Stamler et al. | 514/557 |
| 5,492,904 | 2/1996 | Wong | 514/211 |
| 5,512,681 | 4/1996 | Boswell et al. | 548/300.7 |
| 5,536,723 | 7/1996 | Loscalzo et al. | 514/247 |
| 5,538,991 | 7/1996 | Ashton et al. | 514/397 |
| 5,631,284 | 5/1997 | Legzdins et al. | 514/505 |
| 5,641,793 | 6/1997 | Bradbury | 514/352 |
| 5,958,926 | 9/1999 | Garvey et al. | 514/253 |

OTHER PUBLICATIONS

K. T. Weber et al., "Structural Remodeling in Hypertensive Heart Disease and the Role of Hormones" *Hypertension* 23:869–877 (1994).

D. C. Crawford et al., "Angiotensin II Induces Fibronectin Expression Associated with Cardiac Fibrosis in the Rat" *Circulation Research* 74:727–739 (1994).

D. S. Bredt et al., "Nitric Oxide: A Physiologic Messenger Molecule" *Annu. Rev. Biochem.* 63: 175–95 (1994).

J. Hou et al., "Influence of Nitric Oxide Synthase Inhibition onCardiac Fibrosis Induced by Angiotensin II Infusion", *Circulation* vol. 90, No. 4, Part 2: I–627, Abstract No. 3374 (1994).

*Primary Examiner*—Robert H. Harrison
*Attorney, Agent, or Firm*—Weingarten, Schurgin, Gagnebin & Hayes LLP

[57] ABSTRACT

This invention pertains to the use of a combination of angiotensin inhibitors and nitric oxide stimulators to slow and reverse the process of fibrosis in the body. This combination of medicaments is particularly useful in the treatment of a variety of cardiovascular fibrotic pathologies, such as that associated with left ventricular hypertrophy secondary to hypertension, myocardial infarction, and myocarditis.

6 Claims, No Drawings

COMBINED USE OF ANGIOTENSIN INHIBITORS AND NITRIC OXIDE STIMULATORS TO TREAT FIBROSIS

This is a divisional of application Ser. No. 08/428,819, filed on Jun. 7, 1995 U.S. Pat. No. 5,645,839.

BACKGROUND OF THE INVENTION

1. Field of the Invention

This invention relates to methods and compositions for treating fibrosis. More particularly, the invention relates to the use of angiotensin inhibitors in combination with nitric oxide stimulators to inhibit the progression of fibrosis.

2. Description of the Prior Art

Fibrosis, the formation of excessive amounts of fibrotic or scar tissue, is a central issue in medicine. Scar tissue blocks arteries, immobilizes joints and damages internal organs, wreaking havoc on the body's ability to maintain vital functions. Every year, about 1.3 million people are hospitalized due to the damaging effects of fibrosis, yet doctors have few therapeutics to help them control this dangerous condition. As a result, they often see patients crippled, disfigured or killed by unwanted masses of uncontrollable scars.

Fibrosis can follow surgery in the form of adhesions, keloid tumors or hypertrophic (very severe) scarring. Fibrosis causes contractures and joint dislocation following severe burns, wounds or orthopaedic injuries; it can occur in any organ and accompanies many disease states, such as hepatitis (liver cirrhosis), hypertension (heart failure), tuberculosis (pulmonary fibrosis), scleroderma (fibrotic skin and internal organs), diabetes (nephropathy) and atherosclerosis (fibrotic blood vessels).

Ironically, the very process designed to repair the body can lead to dangerous complications. Like epoxy, scar tissue serves only a structural role. It fills in the gaps, but cannot contribute to the function of the organ in which it appears. For example, as fibrotic scar tissue replaces heart muscle damaged by hypertension, the heart becomes less elastic and thus less able to do its job. Similarly, pulmonary fibrosis causes the lungs to stiffen and decrease in size, a condition that can become life-threatening. Fibrotic growth can also proliferate and invade the healthy tissue that surrounds it even after the original injury heals. Too much scar tissue thus causes physiological roadblocks that disfigure, cripple or kill.

In most cases, fibrosis is a reactive process, and several different factors can apparently modulate the pathways leading to tissue fibrosis. Such factors include the early inflammatory responses, local increase in fibroblast cell populations, modulation of the synthetic function of fibroblasts, and altered regulation of the biosynthesis and degradation of collagen.

One treatment approach, therefore, has been to target the early inflammatory response. Treatment with topical corticosteroids has achieved limited success, if used early in fibrosis. However, steroid therapy has little or no effect once scar tissue has already formed. Furthermore, prolonged administration of hydrocortisone, in pulmonary fibrotic disease for example, may actually worsen the condition.

The second approach involves slowing the proliferation of those cells responsible for the increased collagen synthesis. Generally, this involves fibroblast cells, except in the vasculature where smooth muscle cells are responsible for collagen deposition. Compounds that have been used to inhibit fibroblast proliferation include benzoic hydrazide, as taught by U.S. Pat. No. 5,374,660. Benzoic hydrazide has been shown to suppress collagen synthesis and fibroblast proliferation, at least in tissue culture cells. U.S. Pat. No. 5,358,959 teaches the use of imidazole derivatives to inhibit the growth of fibroblasts by blocking the calcium-activated potassium channel. This particular agent also inhibits the proliferation of endothelial cells and vascular smooth muscle cells.

Likewise, a number of agents which affect smooth muscle cell proliferation have been tested. These compositions have included heparin, coumarin, aspirin, fish oils, calcium antagonists, steroids, prostacyclin, rapamycin, dipyridamole, ultraviolet irradiation, gamma ($\gamma$)-interferon, serotonin inhibitors, methotrexate and mycophenolic acid, either alone or in various combinations.

A number of treatments have been devised that are based on the modulation of the synthetic function of fibroblast or smooth muscle cells. Like most cells, fibroblasts and smooth muscles cells are modulated by cytokines (factors secreted in response to infection that modify the function of target cells). Gamma interferon is a lymphokine (a cytokine that is produced by lymphocytes) known to inhibit fibroblast proliferation and collagen synthesis. Likewise, the monokine (a cytokine that is produced by macrophages) beta-interferon serves the same function. Thus, U.S. Pat. No. 5,312,621 teaches the use of these cytokines in the treatment of fibrosis. Similarly, certain cytokines have been tested for their effect on the proliferation and stimulation of collagen synthesis in smooth muscle cells. For example, U.S. Pat. No. 5,268,358 is directed to the use of peptides that block the binding of platelet-derived growth factors to their receptors. U.S. Pat. No. 5,304,541 is directed to chimeric transforming growth factor-beta (TGF-$\beta$) peptides which block cell proliferation. U.S. Pat. No. 5,308,622 is directed to conjugates comprising fibroblastic growth factor (FGF) and cytotoxic agents. U.S. Pat. No. 5,326,559 is directed to interleukin-2 targeted molecules. Although promising, many of these agents and compositions have known and serious side effects and, consequently, limited effectiveness.

The final treatment strategy involves directly influencing the metabolism of collagen and the other components of fibrotic tissue. Thus, drugs that interfere with the biosynthesis, accumulation and catabolism of collagen have been used in the treatment of fibrosis. Many drugs are used to inhibit collagen synthesis, including derivatives of pyridone, alkadiene, benzoquinone, pyridine, oxalylamino acid and proline analogs. However, all of these drugs suffer from the drawback of also inhibiting the normal, and required, synthesis of collagen as well as the detrimental synthesis that occurs during fibrosis.

One of the most important pathologies for which fibrosis is a contributing factor is cardiovascular disease. Cardiovascular disease is the leading cause of death in the Western world. In the United States it accounted for 930,000 deaths in 1990. There are an estimated 1.5 million heart attacks per year in the U.S. that result in more than 500,000 deaths annually.

One consequence of heart disease is activation of the body's renin-angiotensin-aldosterone system (RAAS). The RAAS system maintains normal fluid volume in the body. The sympathetic nervous system provokes the release of the renin from the kidneys. The release of renin is stimulated by decreased extracellular fluid volume, low renal perfusion and decreased sodium content in the macula densa. Renin is a proteolytic enzyme that acts on angiotensinogen to produce the decapeptide angiotensin I. Angiotensin I is then converted to the octapeptide angiotensin II (AII) by the action of angiotensin-converting enzyme (ACE). AII is a potent pressor agent producing a rapid elevation in blood pressure. AII also plays a role in proliferation of smooth muscle cells.

A particular direct vasodilator is nitric oxide (NO). The use of NO donors is known for decreasing blood pressure in the treatment of angina, ischemic diseases, congestive heart failure, impotence in males, hypertension, arteriosclerosis, cerebral vasospasm, and coronary vasospasm (U.S. Pat. Nos. 4,954,526; 5,278,192).

NO is synthesized by NO synthase (NOS), of which there are several forms. When a dilator such as bradykinin acts at receptors on endothelial cells, the NOS is activated. The newly synthesized NO activates guanylate cyclase, thus producing cGMP. cGMP produces muscle relaxation by mechanisms that are not completely understood, but may involve cGMP-dependent protein kinase phosphorylation of myosin light chain which alters its contractility. NO is also implicated in platelet aggregation and adhesion and functions in various vascular reflexes.

NO therapy is generally achieved by administering drugs, such as nitroglycerine, that donate NO once inside the cell. The rest of the molecule (or NO degradation products) may be metabolically active, thus further complicating the problem of delineating the specific effect of NO on hypertension.

Nitroglycerine (NTG), an NO donor, has been known to be effective in the treatment of angina pectoris since 1879. However, patient tolerance to NTG is a problem, and increasing dosages are often required.

These and other disadvantages of the prior art are overcome by the present invention, and a method and compositions for the treatment of fibrosis is provided.

SUMMARY OF THE INVENTION

In accordance with the present invention, provided herein is a method of treating fibrosis and, more particularly, cardiovascular fibrosis. Also provided are compositions for treating fibrosis and, more particularly, cardiovascular fibrosis.

Therefore, one embodiment of the present invention is a method of treating fibrosis by administering a pharmaceutically effective amount of a combination of at least one angiotensin inhibitor and at least one nitric oxide stimulator, said pharmaceutically effective amount being effective to inhibit or reverse fibrosis. In a preferred embodiment, fibrosis is cardiovascular fibrosis.

More particularly, the cardiovascular fibrosis disease states that can be treated by this method include left ventricular hypertrophy secondary to hypertension, fibrosis associated with myocardial infarction, and/or fibrosis associated with myocarditis.

It is another embodiment of this invention to provide compositions of matter for use in the treatment of fibrosis. The composition comprises a mixture of at least one angiotensin inhibitor, at least one nitric oxide stimulator, and at least one pharmaceutically acceptable carrier. More particularly, the angiotensin inhibitor includes agents such as angiotensin-converting enzyme inhibitors, angiotensin II antagonists, renin inhibitors, angiotensin I inhibitors, angiotensin II receptor antagonists, or activators of angiotensin II catabolism. Furthermore, the nitric oxide stimulator includes agents such as nitric oxide donors, nitric oxide synthase stimulators, or nitric oxide catabolism inhibitors.

More particularly, the combination is administered to a patient by means including pulmonary absorption, injection, topical administration, oral administration, macromolecular targeting or release from an implant.

It is an additional embodiment of this invention to provide a method of reducing the formation of scar tissue comprising contacting the scar tissue with a pharmaceutically effective amount of a combination of at least one angiotensin inhibitor and at least one nitric oxide stimulator, said amount being effective to inhibit or reverse fibrosis.

These and other advantages of the present invention will become apparent from the following detailed description.

DETAILED DESCRIPTION OF THE INVENTION

The present invention provides a method of treating fibrosis by administering a pharmaceutically effective amount of a combination of at least one angiotensin inhibitor and at least one nitric oxide stimulator, said pharmaceutically effective amount being effective to inhibit or reverse fibrosis. In a preferred embodiment, fibrosis is cardiovascular fibrosis.

More particularly, the cardiovascular fibrosis disease states that can be treated by this method include left ventricular hypertrophy secondary to hypertension, fibrosis associated with myocardial infarction, and/or fibrosis associated with myocarditis.

It is another embodiment of this invention to provide compositions of matter for use in the treatment of fibrosis. The composition comprise a mixture of at least one angiotensin inhibitor, at least one nitric oxide stimulator, and at least one pharmaceutically acceptable carrier. More particularly, the angiotensin inhibitor includes agents such as angiotensin-converting enzyme inhibitors, angiotensin II antagonists, renin inhibitors, angiotensin I inhibitors, angiotensin II receptor antagonists, or activators of angiotensin II catabolism. Furthermore, the nitric oxide stimulator includes agents such as nitric oxide donors, nitric oxide synthase stimulators, or nitric oxide catabolism inhibitors.

The term "angiotensin inhibitor" means an agent that interferes with the function, synthesis or catabolism of angiotensin II (AII). These agents include, but are not limited to, angiotensin-conversion enzyme (ACE) inhibitors, AII antagonists, AII receptor antagonists, agents that activate the catabolism of AII, and agents that prevent the synthesis of angiotensin I from which AII is ultimately derived. Suitable ACE inhibitors include, but are not limited to, captopril, enalapril, enalaprilat, lisinopril, ramipril, zofenopril, ceranapril, alacepril, delapril, pentopril, quinapril, rentiapril, duinapril, spirapril, cilazapril, perindopril, and fosinopril. Suitable AII antagonists include, but are not limited to, saralasin. Suitable angiotensin II receptor antagonists include, but are not limited to, losartan. Suitable agents that prevent the synthesis of angiotensin I from which AII is ultimately derived include, but are not limited to, renin inhibitors.

The term "nitric oxide (NO) stimulator" means an agent that acts to produce increased levels of NO. Suitable agents include, but are not limited to, NO donors, NO synthase (NOS) stimulators, and NO catabolism inhibitors. Suitable NO donors include, but are not limited to, nitroglycerin, amyl nitrate, nitroprusside, isosorbide dinitrate, erythityl dinitrate, nonoates and pentaerythritol tetranitrate. Suitable NOS stimulators include, but are not limited to, bradykinin, acetylcholine, thrombin, histamine and substance P. Suitable NO catabolism inhibitors include antioxidants, such as, but not limited to, ascorbate, tocopherol and β-carotene.

As used herein, the term "fibrosis" means those disorders or disease states that are caused by the abnormal deposition of scar tissue. Fibrosis includes, but is not limited to, cardiovascular fibrosis such as that associated with left ventricular hypertrophy, myocardial infarctions, and myocarditis. Fibrosis also includes all arteriosclerotic disorders. Fibrosis also includes pulmonary fibrosis, adult respiratory distress syndrome, inflammatory disorders, sclerodermas, cirrhosis, keloids, and hypertrophic scars.

In one embodiment of the present invention, the combination of angiotensin inhibitor and NO inhibitor is administered along with a pharmaceutically acceptable carrier. In another embodiment, the combination of angiotensin inhibitor and NO inhibitor is co-administered with one or more agents selected from the group consisting of diuretics, cardiac glycosides, phosphodiesterase inhibitors, anti-anginal agents, anti-arrhythmic agents, calcium channel, blocking agents, peripheral vasodilators, thrombolytic agents, potassium channel activators, anticoagulants, vasopressors, beta-adrenergic blockers, alpha-adrenergic blockers, antihypertensives, potassium-removing resins, cardioplegic solution, anti-hyperlipidemic agents, and edetate disodium, with a pharmaceutically acceptable carrier. Additionally, the therapeutic combination of the present invention may be combined with other treatments. For example, the compounds may be combined with one or more cardiovascular agents selected from diuretics, cardiac glycosides, phosphodiesterase inhibitors, anti-anginal agents, anti-arrhythmic agents, calcium channel-blocking agents, peripheral vasodilators, thrombolytic agents, potassium channel activators, anticoagulants, vasopressors, beta-adrenergic blockers, alpha-adrenergic blockers, antihypertensives, potassium-removing resins, cardioplegic solution, anti-hyperlipidemic agents, edetate disodium and the like.

The compounds of the instant invention may be prepared in known formulations and administered accordingly. Examples of such formulations include, but are not limited to, tablets, coated tablets, capsules, granules, aerosols, syrups, emulsions, suspensions, solutions, and ointments with pharmaceutically acceptable excipients or solvents. The active compounds should be present in a concentration of about 0.5% to 90% by weight of the total mixture, i.e., in amounts sufficient to achieve the dosage range indicated.

A variety of acceptable additives may be employed, including, but not limited to, emulsifiers, dispersants, suspending agents, disintegrators, lubricants, binders, and the like. Formulations may also include antioxidants, preservatives, stabilizers, and the like. Diluents, buffering agents, moistening agents, flavoring agents, coloring agents, and the like may also be included.

It is to be understood that the choice of formulation may vary depending on the specific compound utilized. For example, nitroglycerine is typically provided in transdermal patch, tablet, or ointment form. Some compounds are known to be light sensitive, while others have a short half-life or absorb to plastic. Certain peptide AII antagonists are known to be least efficacious when taken orally. The choice of formulation will accommodate such limitations. Furthermore, certain compounds may be incompatible in a particular formulation, thus necessitating the separate administration of such compounds.

It is known that some NO donors exhibit varying degrees of tolerance which may necessitate intermittent administration of such compounds. For this reason, it may be beneficial to employ organic nitrites which induce less tolerance. Alternatively, it may be preferable to co-administer other agents which help to alleviate the tolerance problem, such as sulfhydryl donors, or to employ agents that stimulate NOS production in vivo, or serve as a substrate for NOS. Such agents include those that stimulate NOS, and those that inhibit the catabolism of NO or feedback inhibition of NOS.

Dosage of these compounds may be titered as that dosage sufficient to achieve the desired effect, i.e., inhibition or reversal of fibrosis. The ratio of one compound to the other may be determined by pharmacokinetic principles known to those skilled in the art. In general, doses will be comparable to those used in hypertension or congestive heart failure.

In spite of this, it may be necessary to deviate from the amounts mentioned, depending on the body weight, type and timing of administration, type of formulation, characteristics of the compounds used, and the severity of disease and side effects. These amounts can be determined by pharmacokinetic principles well known to those skilled in the art. Thus, in some cases it may be possible to use less than the above-mentioned amounts, while in other cases additional amounts will be required.

The following examples serve to illustrate specific embodiments of the invention, but should not be considered as a limitation on the scope of the invention.

EXAMPLE 1

This example shows that NO profoundly affects the progression of fibrosis in the cardiovasculature. It is demonstrated that the NOS inhibitor N-nitro-L-arginine-methyl ester (L-NAME) influences the effect of AII on the cardiovasculature.

L-NAME was given to adult Wistar rats in drinking water (40 mg/kg/day) for between 4–40 days. Fibrosis was characterized by quantitating immuno-detectable fibronectin, the presence of inflammatory cells within interstitial and perivascular spaces and the steady state levels of mRNA for matrix genes and atrial natriuretic factor (ANF). Although blood pressure was maintained at high levels because of the lack of endogenous NO, cardiac hypertrophy or fibrosis was not observed, even after 2 weeks. If AII was given at a pressor dose after 2 weeks of L-NAME treatment, a marked fibrosis was observed that was far more severe than that seen with AII alone. However, this fibrosis did not occur if AII was administered shortly after L-NAME treatment was initiated. A sub-pressor dose of AII administered for 3 days produced only mild fibrosis. However, when administered to a rat pretreated for 2 weeks with L-NAME, the sub-pressor dose of AII caused significant fibrosis. These data indicate a counter-regulatory role for NO in modulating the AII-induced cardiac fibrosis and suggest a potentially important autocrine or paracrine role for NO in fibroblast proliferation. The table summarizes physiological parameters and densitometric data of the mRNA levels for marker genes obtained using Northern blot analyses. The groups summarized include control rats, animals given either L-NAME alone for 17 days, angiotensin II alone for 3 days, or both drugs together, the angiotensin II being administered during the final 3 days of L-NAME treatment. Also included are drug treatments with an angiotensin II receptor antagonist (losartan) or L-arginine, a substrate for nitric oxide synthase thought to increase NO production in vivo. Blood pressure changes were most pronounced when L-NAME was given, and drug treatment did not normalize the hypertension. Heart weight/body weight ratios were increased with combined treatment of L-NAME and ang II, and this change was only partly modulated by giving either losartan or L-arginine. Fibronectin mRNA, which is an excellent index of early fibrosis, increased most dramatically in the 3-day treatment period when ang II was given to L-NAME-treated rats, the average increase being more than 50-fold that of control levels. Fibrillar collagen (Type III) also increased dramatically, and atrial natriuretic factor (ANF), a marker for myocyte hypertrophy, also was obviously affected by the combined treatment. When losartan was given at a relatively high dose of 20 mg/kg/day, there was a greater suppression of gene expression than was observed with 10/mg/kg/day, suggesting that in this model, inhibition was not accomplished at doses that would normally suppress the effects of higher amounts of angiotensin II in the absence of L-NAME treatment. Administration of L-arginine during the latter 10 days of treatment at a dose of 4 g/kg/day also markedly attenuated the response to combined treatment. Thus, both an angiotensin receptor antagonist and a potential substrate for nitric oxide synthase modulated the fibrotic response.

TABLE 1

Effect of Drug Treatment on Blood Pressure, Heart Weight and Body Weight

| Treatment Groups | Number of Animals | Systolic Blood Pressure (mm Hg) | Heart Weight/ Body Weight (× 1000) | Relative Change in Steady State mRNA Level | | |
|---|---|---|---|---|---|---|
| | | | | Fibronectin | Type III Collagen (fold increase) | ANF |
| Control (17 days) | 8 | 132 ± 2 | 2.86 ± 0.1 | 1 | 1 | 1 |
| L-NAME (17 days) | 6 | 183 ± 9 | 2.77 ± 0.1 | 1.1 ± 0.1 | 1.1 ± 0.1 | 1.0 ± 0.1 |
| Ang II (3 days) | 7 | 148 ± 10 | 3.04 ± 0.1 | 1.4 ± 0.2 | 1.2 ± 0.1 | 1.6 ± 0.2 |
| L-NAME + ang II | 10 | 186 ± 5 | 3.52 ± 0.1 | 55 ± 7.2 | 9.0 ± 1.3 | 14.6 ± 3.5 |
| L-NAME + ang II + losartan (10 mg/kg/day) | 6 | 182 ± 7 | 2.80 ± 0.1 | 13.7 ± 5.2 | 6.3 ± 3.2 | 10 ± 7.1 |
| L-NAME + ang II + losartan (20 mg/kg/day) | 6 | 169 ± 3 | 2.72 ± 0.1 | 6.8 ± 2.2 | 1.8 ± 1.4 | 1.6 ± 0.5 |
| L-NAME + ang II + L-arginine (4 g/kg/day) | 6 | 172 ± 7 | 2.74 ± 0.1 | 13.5 ± 3.2 | 1.8 ± 1.2 | 5.4 ± 1.1 |

All data are expressed as mean ± standard error.
All changes in steady-state mRNA levels, were expressed relative to that of control values.

Many other variations and modifications may be made in the methods and compositions herein-described, by those having experience in this art, without departing from the concept of the present invention. Accordingly, it should be clearly understood that the methods described in the foregoing description are illustrative only, and not intended as a limitation on the scope of the invention.

What is claimed is:

1. A composition consisting of a combination of an angiotensin inhibitor, a nitric oxide stimulator, and a pharmaceutically acceptable carrier.

2. The composition according to claim 1, wherein the angiotensin inhibitor is one or more agents selected from the group consisting of angiotensin-converting enzyme inhibitors, angiotensin II antagonists, renin inhibitors, angiotensin I inhibitors, angiotensin II receptor antagonists and activators of angiotensin II catabolism.

3. The composition according to claim 2, wherein the angiotensin-converting enzyme inhibitor is selected from the group consisting of captopril, enalapril, enalaprilat, lisinopril, ramipril, zofenopril, ceranapril, alacepril, delapril, pentopril, quinapril, rentiapril, duinapril, spirapril, cilazapril, perindopril, and fosinopril.

4. The composition according to claim 2, wherein the angiotensin II receptor antagonist is losartan.

5. The composition according to claim 1, wherein the nitric oxide stimulator is one or more agents selected from the group consisting of nitric oxide donors, NO synthase (NOS) stimulators, and NO catabolism inhibitors.

6. The composition according to claim 3, wherein the nitric oxide donor is selected from the group consisting of nitroglycerin, amyl nitrate, nitroprusside, isosorbide dinitrate, erythityl dinitrate, and pentaerythritol tetranitrate.

* * * * *

UNITED STATES PATENT AND TRADEMARK OFFICE
CERTIFICATE OF CORRECTION

PATENT NO. : 6,139,847
DATED : October 31, 2000
INVENTOR(S) : Aram Chobanian et al.

It is certified that error appears in the above-identified patent and that said Letters Patent is hereby corrected as shown below:

Column 1,
Line 7, prior to "BACKGROUND OF THE INEVENTION", please insert the following paragraph:
-- STATEMENT REGARDING FEDERALLY SPONSORED RESEARCH OR DEVELOPMENT This invention was made with government support under Contract No. HL47124 awarded by the National Institutes of Health. The government has certain rights in the invention. --

Signed and Sealed this

Twenty-ninth Day of January, 2002

Attest:

*Attesting Officer*

JAMES E. ROGAN
*Director of the United States Patent and Trademark Office*